Figure 1:
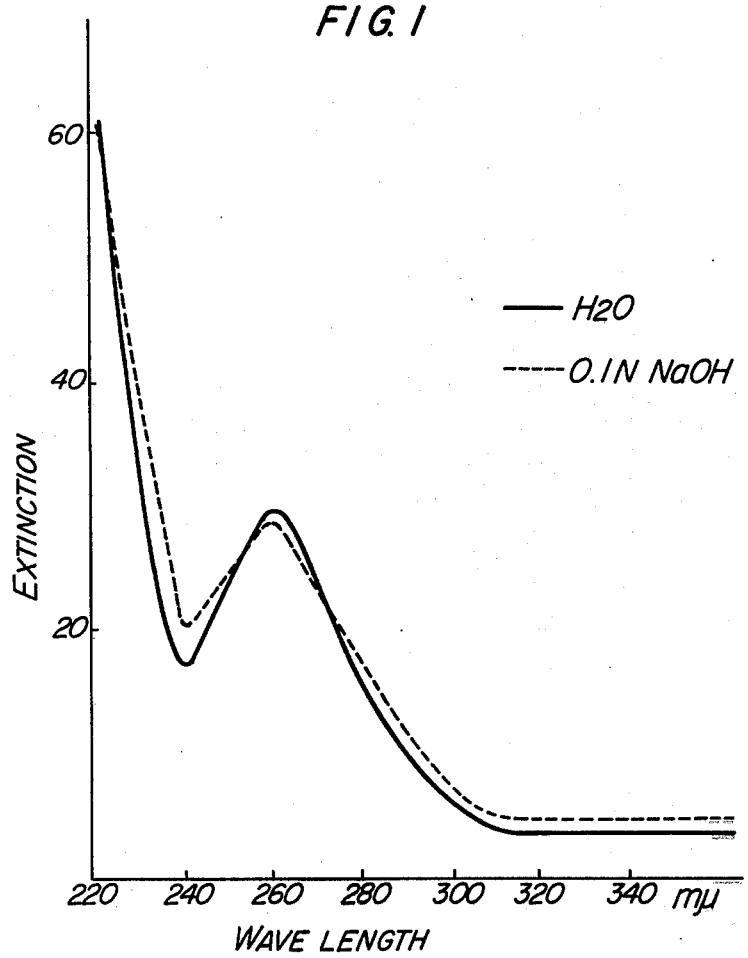

United States Patent [19]

Ishida et al.

[11] 3,980,776

[45] Sept. 14, 1976

[54] COMPOSITION CONTAINING DOUBLE STRANDED RNA FROM BASIDIOMYCETES AND METHOD OF USE

[75] Inventors: Nakao Ishida; Mikio Kikuchi, both of Sendai, Japan

[73] Assignee: Nakao Ishida, Sendai, Japan

[22] Filed: Mar. 13, 1975

[21] Appl. No.: 557,971

Related U.S. Application Data

[62] Division of Ser. No. 37,698, May 15, 1970, Pat. No. 3,907,778.

[30] Foreign Application Priority Data

May 26, 1969 Japan.................................. 44-40404

[52] U.S. Cl................................. 424/181; 424/85; 424/180

[51] Int. Cl.² ................ A61K 31/715; A61K 45/02; A61K 31/70

[58] Field of Search............ 424/85, 181; 260/211 R

[56] References Cited

UNITED STATES PATENTS

| | | | |
|---|---|---|---|
| 3,629,235 | 12/1971 | Lampson et al. ...................... | 424/85 |
| 3,719,754 | 3/1973 | Day et al. .............................. | 424/85 |
| 3,819,482 | 6/1974 | Vidaver et al. ........................ | 424/85 |
| 3,852,423 | 12/1974 | Nakase et al. ........................ | 424/85 |

*Primary Examiner*—Sam Rosen
*Attorney, Agent, or Firm*—Stevens, Davis, Miller & Mosher

[57] ABSTRACT

An inducer of interferon for the viral infection composed mainly of double stranded RNA is extracted and isolated from spore or mycelium of natural or cultivated basidiomycetes such as *Cortinellus Shiitake*.

9 Claims, 5 Drawing Figures

COMPOSITION CONTAINING DOUBLE STRANDED RNA FROM BASIDIOMYCETES AND METHOD OF USE

This is a division of application Ser. No. 37,698, filed May 15, 1970, now U.S. Pat. No. 3,907,778.

This invention relates to an inducer of interferon for viral infection and to its manufacturing method.

In more particulars, this invention relates to the new substance by which the resistant substance peculiar to the individual body is induced in the body, against various viral infection in human beings, animls and birds and the new substance prevents with certainty the development of symptoms resultant from the viral infection. The invention also covers its manufacturing method through isolation.

The viral diseases of human beings, animals or birds are always infections and could become pandemic at a region or in the world within a short span of time. This is evidenced in the worldwide epidemics in the past such as influenza, and small-pox. It is clear that such epidemics not only caused a great loss of life but also meant an immense damage to the social and economic assets of mankind.

On the other hand, the rapid progress in the techniques of tissue culture and virology has resulted in the intensified worldwide research for the prophylaxis and therapy of viral infections. However, no practical prophylactic or therapeutic means have been developed so far against the viral infections except for the use of vaccine. Even vaccination still has many problems to be solved in regard to the side effects.

Meanwhile, through the study by Joel Warren et al. (U.S. Pat. No. 29,002 of 1968), it is known that nucleic acid extracted from non-viral yeast and some bacteria (the name is not known), and DNA from calf thymus are effective to viral infections, since they induce resistant substances to virus. These inducive bodies (which are called "inducers" here) induce resistant substances (which are called "interferon" here). The kind of interferons and its formation processes are different. The difference is caused also by the kind of inducers and the effects are accordingly not the same either. Even if they are non-viral nucleic acid, only some of them can function as inducer. (In fact, DNA of colitis germs, DNA of human leucocyte, all RNA of Hela cells etc, show no function at all. Even as to the above calf thymus DNA, the repeated test failed to confirm the effect).

The appearance of more effective inducer and shorter inductive period has been therefore looked forward to.

However, only scarce knowledge has so far been obtained as to what kind of substance is suitable for this purpose. Only 2 years ago, M. R. Hilleman et al. discussed the basic principle, suggesting that double stranded ribonucleic acid may have the interferon formation function.

Moreover, the existence of double stranded RNA is not known with exception of a few cases. Its existence is only considered possible in bacteriophage, etc., where RNA virus is found as parasite.

In view of such circumstance, the present inventors had been engaged in the development of prophylactic and therapeutic agents to the viral infectious cases in animals. As the result, the present inventors have found that spore and mycelium of a number of basidiomycetes, where the existence of double stranded RNA was not expected at all, contain a substance which can prevent the infection of animal influenza, variola, New Castle disease and many other viral diseases, and further can inhibit the development of subsequent symptoms.

The present inventors have succeeded in extracting this substance and also in isolating the effective component. Further, the present inventors confirmed that the structure is double stranded RNA and that the mechanism of action is based on the formation of interferon specific to the individual body.

The immunity acquired by vaccination is effective only specifically for the limited antigen. Therefore, the vaccination of rhino-virus, adeno-virus, entero-viruses, etc. which have multiantigenecity cannot be practically employed for all types of antigens. Furthermore, the viral antigen is not always the superior immunity agent. In addition, it takes a considerable time to increase the antibody titre after the vaccination, during which time no therapeutic effect is expected.

On the contrary, the substance existing in basidiomycetes discovered by the present inventors, when administered at the amount of 1–8 mg/kg in terms of the crude substance after extraction, can induce a powerful inhibitory substance on viral infection of animal in a short time span of 1–2 hours. Besides, the inhibitory substance itself of this invention is very stable. Furthermore, the resistant property obtained with the substance of the present invention is not specific to one virus, which is different from vaccines, and the remarkable effect is shown in all viral infectious cases.

In order to obtain the substance of this invention, the spore and mycelium of basidiomycetes collected from the natural field or cultivated artificially are crushed. Then the crude substance, containing double stranded RNA, is easily obtained by applying the publicly known separation method for nucleic acid, etc., for example, extraction by means of saline solution and/or centrifugal separation by use of phenol.

This crude substance can be sufficiently used as it is. However, if the effective component is desired from this crude substance, such fraction has only to be taken as corresponds to double stranded RNA fraction by use of ordinary column chromatography, etc.

For example, it is possible to obtain pure double stranded RNA by means of dissolution in saline solution containing buffer, using DEAE cellulose.

As to the substance of this invention which is obtainable as above, it was proven from the following that double stranded RNA is the effective substance; namely, the position of diffused fraction in the above chromatography, the susceptibility to RNase as shown in Reference 1 and the position of effective fraction obtained in density gradient centrifugation as shown in Reference 2.

Concerning the interferon, or the substance induced by the material of this invention, Reference 3 confirms its formation process and efficacy, Reference 4 relates to its molecular weight in the case of rabbit, Reference 5 describes its thermal stability, Reference 6 covers the equipotential point, and Reference 7 refers to the species specificity.

Furthermore, the substance of this invention shows no toxicity at all in animals and inhibits the viral infection with high reproducibility, without indicating the virucidal activity.

The resistance inducing activity to viral infection by the substance of this invention is found most remarkable when this substance is administered to animals before the viral infection. Accordingly, it will be more adequate to use this substance as prophylactic agent against viral infection. However, it can be also effectively applied for therapeutic purpose as is evidenced in the examples.

The additional explanation of this invention will be further made with reference to the examples and referential cases. However, it is not intended to limit the invention to these examples. Mol means mole concentration.

EXAMPLE 1

1 g. of spore or mycelium of *Cortinellus Shiitake* was sufficiently crushed by means of sea sand, Waring blender, omni-mixer, etc. Then, 30 ml. of LTM buffer solution containing 0.2 % EDTA was added thereto, followed by 30 ml. water-saturated phenol. Strong agitation was continued for 5 minutes in water. This suspension was subjected to the centrifugation under 3,000 rpm for 5 minutes, and was divided into aqueous layer and phenol layer. The substance of this invention was contained in the aqueous layer. The aqueous layer was washed three times with 60 ml. of water-saturated phenol. Then, 75 ml. of ether was added. Further, nitrogen gas was charged into 24 ml. of this aqueous layer in order to remove ether. 125 ml. of cold ethanol was added thereto and the solution was left for 18 hours at 4°C. By this procedure, white powder weighing ca. 32 mg/dry weight was obtained.

This powder distinctively inhibited the influenza virus infection in animal at the concentration of less than 0.1 mg/kg. No toxicity to animal was observed at all, in the case of mouse, at 500 mg/kg.

The UV absorption spectrum of the substance of this invention is shown in FIG. 1. Since it shows the strong absorption at 260 m$\mu$, the substance of this invention is believed to be ribonucleic acid.

EXAMPLE 2

DEAE cellulose column chromatography was effected to the powder obtained in Example 1. Sufficiently activated cellulose was filled into 2.2 x 24 cm. column by use of $N_2$ gas and was bufferized with 0.005 mol tris-hydrochloric acid buffer containing 0.1 mol sodium chloride and 0.01 Mol EDTA (ethylenediaminetetraacetate). Then 10 mg. of powder obtained in Example 1 was dissolved into 2 ml. of the solution already used for buffer, and was added on the top of column, and 160 ml. of the buffer solution was flowed therethrough. The saline concentration was then increased straightly up to 1 mol. Finally, elution was effected with 3 Mol saline solution.

Figure 2:
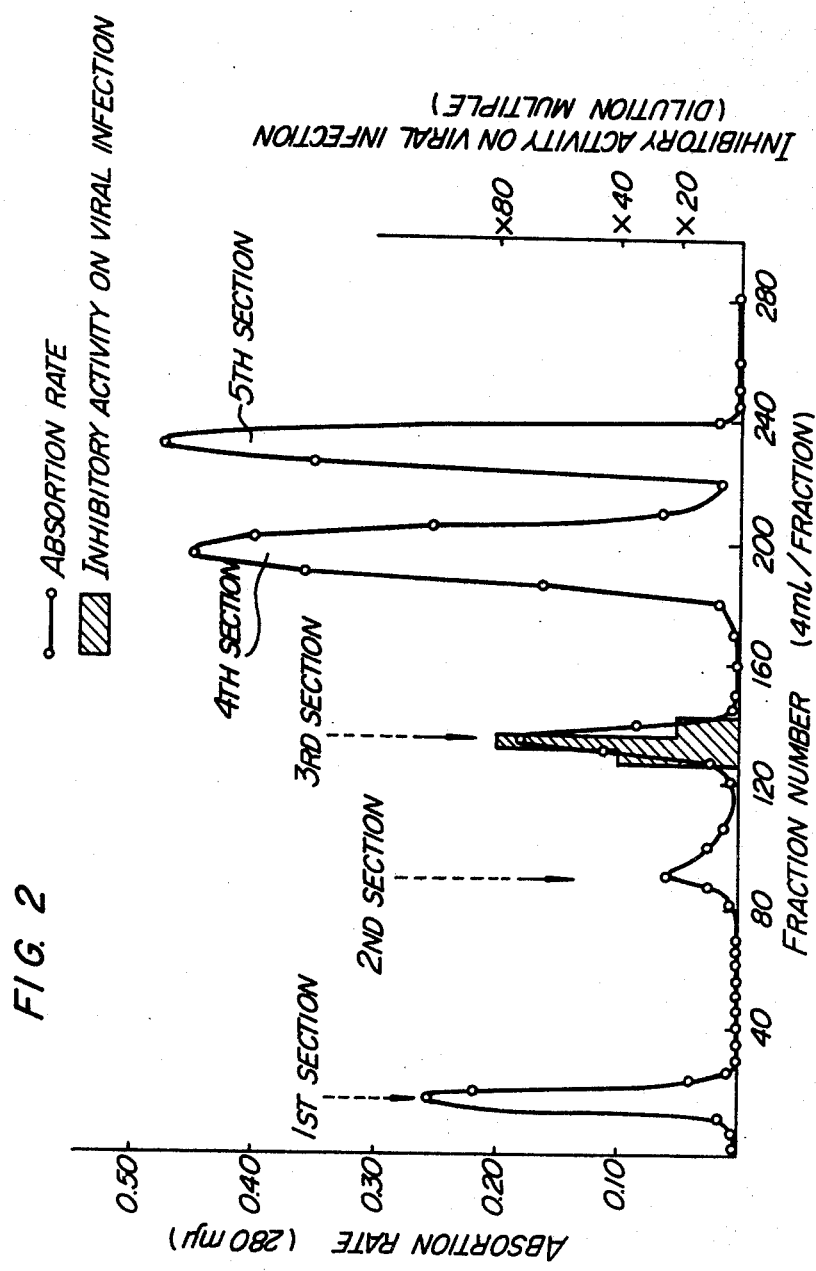

The primary cultured cells of rabbit kidney were pre-treated for 24 hours respectively with 5 sections which were obtained by measuring 260 m$\mu$ absorption degree. The cells were washed then twice in the culture medium. Then it was infected with vesicular stomatitis virus at 100 TCD 50/ml. and, after 24 hours cultivation, it was inspected with microscope in order to examine its inhibitory activity on viral infection. The result, indicated in FIG. 2, shows the inhibitory activity on the third section covering 130 –140 fractions. The position of fraction suggests that the substance is double stranded RNA.

EXAMPLE 3

Forty mice of dd strain weighing 11 to 13 g. were infected with influenza virus intranasally as the control group.

Two dosage levels of crude substance obtained in Example 1 were given to the test group treated in the same manner as the above control group.

Meanwhile, amantadine was administered to the positive control group in order to investigate the survival day and survival rate. RNA fraction and amantadine were dissolved into saline, and administered intraperitoneally in 14 divided dosages i.e., 1 hour before viral infection, at the same time as infection, 1, 3, 6 hours after infection, and twice a day in the following 4 days.

The mice were infected with 5 $LD_{50}$ of influenza virus A/swine by intra-nasal inoculation. The result is summarized in Table 1.

Table 1

| Treatment | Number of animals | Average survival days | Survival rates (%) |
|---|---|---|---|
| Control | 40 | 9.11 | 7.5 |
| Substance of the present invention | | | |
| 8 mg/kg | 21 | 13.30 | 70 |
| 4 mg/kg | 10 | 12.10 | 52.4 |
| Amantadine | | | |
| 8 mg/kg | 10 | 9.60 | 14.2 |

As shown in Table 1, the animals treated with the substance of this invention clearly indicates the remarkable enhancement of the survival rate in comparison with the non-treated control group.

EXAMPLE 4

Crude substance obtained in Example 1 was administered to the mouse once intraperitoneally at the dosage of 8 mg/kg and 4 mg/kg. One hour later, $5LD_{50}$ of influenza A/Swine was infected. The result is summarized in Table 2.

Table 2

| Treatment | Number of animals | Average Survival days | Survival rates (%) |
|---|---|---|---|
| Control | 22 | 8.6 | 0 |
| Substance of the present invention | | | |
| 8 mg/kg | 11 | 12.1 | 54.0 |
| 4 mg/kg | 11 | 10.9 | 36.0 |
| Amantadine | | | |
| 8 mg/kg | 10 | 9.3 | 10.0 |

Judged from the Table 2, the substance of this invention is as effective by one administration before the viral infection as the case of Example 3. This result indicates that this substance induces the resistance to the viral infection.

EXAMPLE 5

Further purified substance obtained in Example 2 was tested on mouse Mengs virus infection in mice. A solution of the test substance was administered intraperitoneally 18 hours pre-infection at the dosages of 20, 2 and 0.2 mg/kg. The result is summarized in Table 3.

Table 3

| Dose (mg/kg) | Survival rates (%) |
|---|---|
| 20 | 60 |
| 2 | 50 |
| 0.2 | 70 |

Significant protection was obtained even at 0.2 mg/kg, although all mice with saline died.

EXAMPLE 6

Mouse pneumonitis virus challenge study was performed with the same substance as in Example 5. The substance was administered in mice intranasally 18 hours pre-infection Table 4 summarizes the data obtained in this study.

Table 4

| Dose (mg/kg) | Survival rates (%) |
|---|---|
| 1.5 | 40 |
| 0.2 | 0 |
| 0.02 | 0 |
| 0.002 | 0 |

40 % Survival was obtained at 1.5 mg/kg by the intranasal administration.

REFERENCE 1

About the powder obtained in Example 1, the enzyme susceptibility under various salt concentrations was examined. Saline solution was prepared in 2 concentrations of 0.01 mol and 0.3 mol. 0.05 mol Tris-buffer solution containing 0.001 mol EDTA, RNase (20 mcg./ml. and 1.0 mcg/ml., 2 concentrations) and the substance of this invention were added thereto. The third group buffer contained only RNase. They were incubated in the aqueous solution for 30 minutes at 37°C. Then, as in Example 2, viral infection inhibitory activity, which remained in the buffer solution, was examined by use of the primary cultured cells of rabbit kidney. The result is summarized in Table 5.

The result of Table 5 shows, as that of Example 2, that the substance of this invention is double stranded RNA.

Table 5

| Saline concentration (Mol) | RNase (mcg/ml) | Substance of the present invention (mcg/ml) | Residual inhibitory activity on viral infection |
|---|---|---|---|
| | 20.0 | 1,000 | 50 |
| | 1.0 | 1,000 | 100 |
| 0.3 | 0 | 1,000 | 100 |
| | 20.0 | 0 | <10 |
| | 1.0 | 0 | <10 |
| | 0 | 0 | <10 |
| | 20.0 | 1,000 | <10 |
| 0.01 | 1.0 | 1,000 | <10 |
| | 0 | 1,000 | 100 |
| | 20.0 | 0 | <10 |

*indicated by the maximum effective dilution multiple of supernatant.

REFERENCE 2

Figure 3:
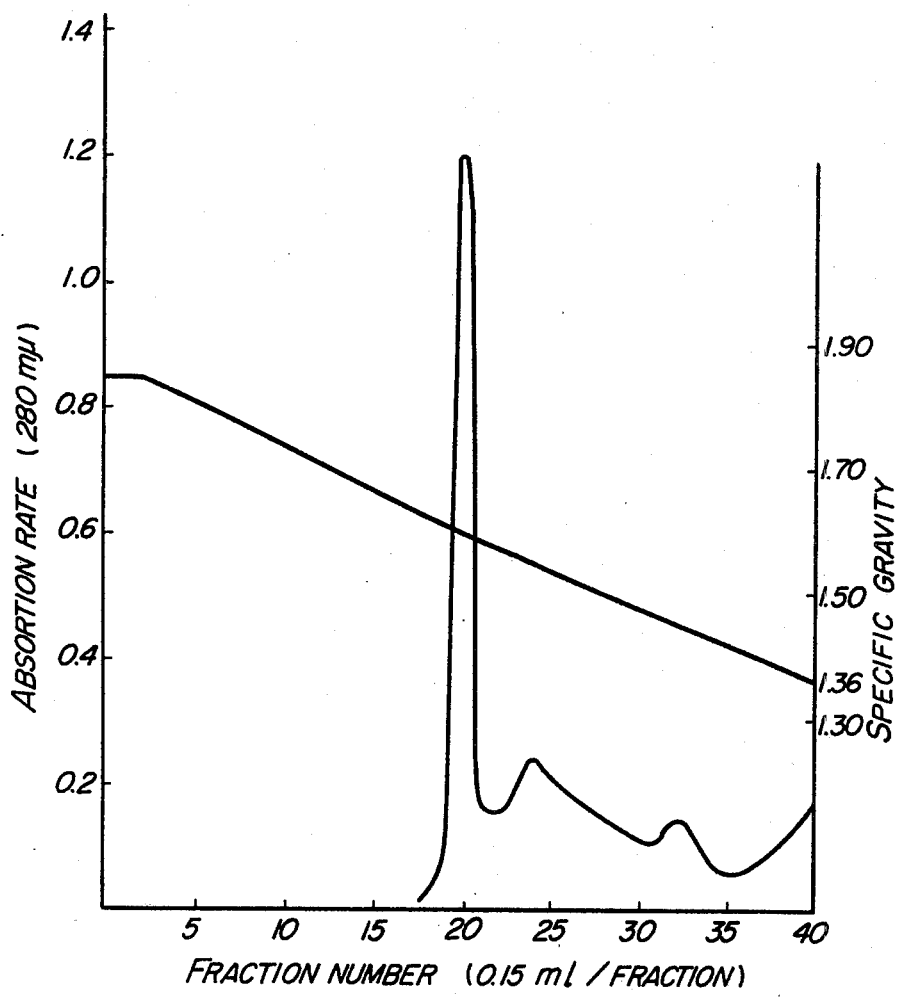

4.5 ml. of cesium sulfate ($Cs_2SO_4$) adjusted at the specific gravity of 1.617 and 1 mg. of the powder obtained in Example 1 were mixed with 0.5 ml. of 0.05 mol Tris-hydrochloric acid buffer solution containing 0.1 mol NaCl and 0.001 mol EDTA. Then the resultant solution was transferred into 5 ml. vessel made of nitrocellulose, followed by the centrifugation at 40,000 rpm for 108 hours by use of Hitachi 55 P-2 type preparative ultracentrifuge using swing rotor. After the centrifugation, a hole was made with pin at the bottom of the nitrocellulose vessel and each 4 drops of solution were taken into the separate test tubes for the measurement of specific gravity as to the respective fraction. Then each fraction was diluted with 0.05 mol Tris-buffer solution containing 0.1 Mol sodium chloride and 0.005 mol EDTA, and the absorption at 260 m$\mu$ was measured. Then, as in Example 2, the viral infection inhibitory effect was examined. The result is shown in FIG. 3.

As the result indicates, viral infection inhibitory activity is observed at the peak obtained in the fraction with the specific gravity of 1.61 (the 20th fraction). The substance to be obtained at the specific gravity of ca. 1.61 is generally double stranded riboneucleic acid. Therefore, the substance of this invention is thought to be double stranded riboneucleic acid.

REFERENCE 3

To 4 rabbits weighing 2 kgs. per group, 1 mg/rabbit of the crude substance of this invention was injected through the otic vein as the treated group. Examination on the viral infection inhibitory activity to be induced by the substance of this invention was made.

As the positive control group, 4 rabbits were administered with 0.1 mg. of inosinic acid-cytidylic acid copolymer (Poly I:C) at the ratio of 0.1 mg. per rabbit via otic vein. Further, other 4 rabbits were administered with saline as control group.

As to each group, the blood was taken at 2, 4 and 6 hours after the administration from the otic vein. The blood was subjected to the centrifugation at 3,000 rpm for 5 minutes to separate the serum. The quantitative analysis of viral infection inhibitory substance induced in the rabbit serum was carried out in accordance with the method of Example 2.

The result is indicated in Table 6. Judged therefrom, the resistance to the viral infection induced in the animal body by the substance of this invention is estimated to come from the viral inhibitory factor (interferon).

Table 6

| Treatment | Viral infection inhibitory activity after administration | | | |
|---|---|---|---|---|
| | 2 hrs | 4 hrs | 6 hrs | 8 hrs |
| Substance of the present invention (0.5 mg/kg) | 1600 | 400 | 400 | 200 |
| Poly I:C (positive control group) | 6400 | 3200 | 1600 | 400 |
| Physiological saline solution (control group) | <10 | <10 | <10 | <10 |

Remarks: The figures shown above is the serum maximum dilution which indicates viral infection inhibitory activity.

REFERENCE 4

Examination was made of the inhibitory substance (interferon) against viral infection produced in rabbit serum by the substance of this invention.

The substance of this invention was administered to the rabbit weighing ca. 2 kg. by route of otic vein and the blood was taken from otic vein after 2 hours. The blood was subjected to the centrifugation for 5 minutes at 3,000 rpm.

Figure 4:
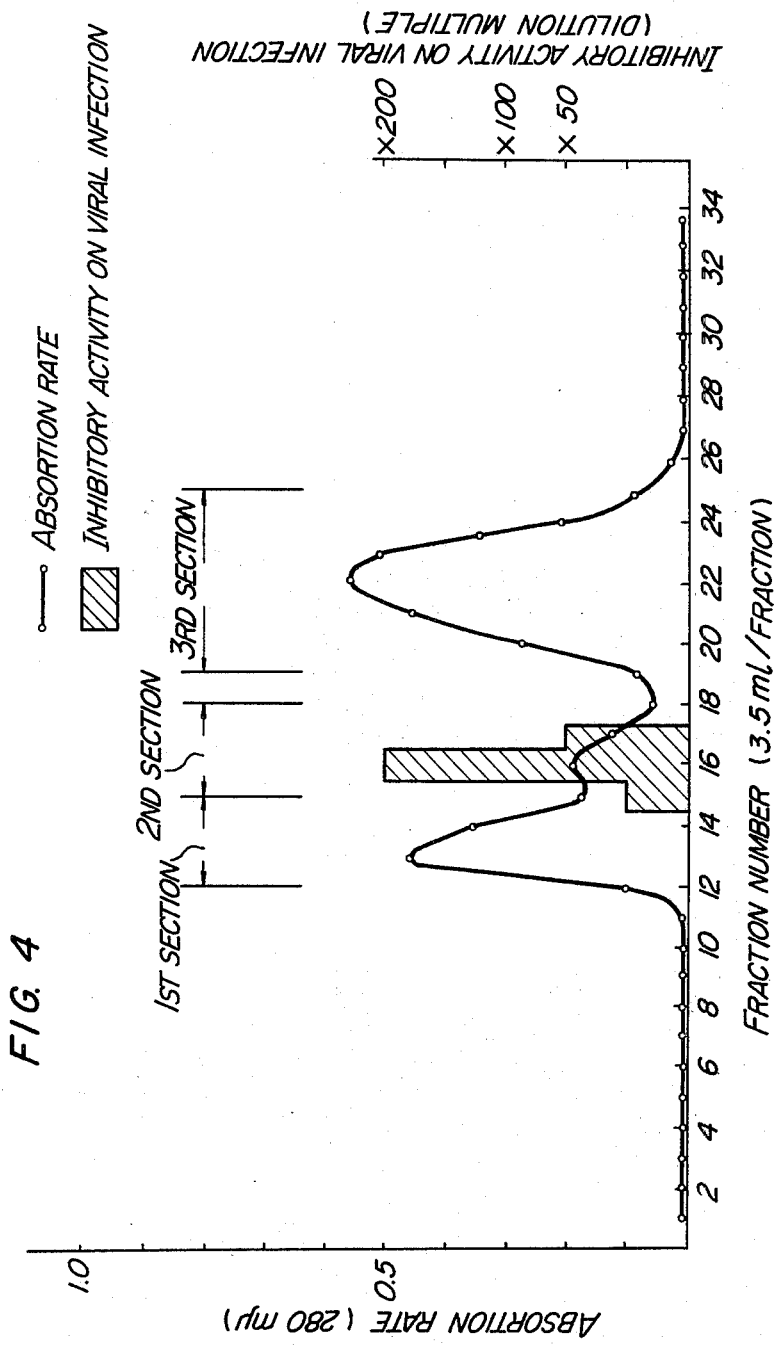

Meanwhile Sephadex G-100 column (1.4 × 120 cm.) was prepared which was equilibrated for 4 days with 0.005 mol Tris-hydrochloric acid buffer solution containing 0.1 mol NaCl and 0.01 mol EDTA. 1.5 ml. of the above-mentioned rabbit serum was added into the column and the gel filtration was made. In this elution, the same buffer solution was used as was employed in the equilibration of Sephadex. Fractionation was made as to each 3.5 ml. employing the fraction collector of LKD Company and the absorption rate at 280 mμ was measured at the same time. Every 2 fractions, the qualitative and quantitative analyses were made as to the viral infection inhibitory substance. These qualitative and quantitative analyses were effected in accordance with the procedures of Example 2. The result is shown in FIG. 4. The viral infection inhibitory activity was observed in the 16th fraction (2nd section). The 1st section (12th – 15th fraction) is for globulin fractions (molecular weight: more than 100,000), and the 3rd section (19th – 25th fraction) is for albumin fraction (molecular weight: ca. 60,000). Further, Ka value of 16th fraction in this gel filtration corresponds to 0.43.

Accordingly, the viral infection inhibitory substance induced in the rabbit serum by the substance of this invention is considered to be protein having the molecular weight of ca. 70,000 – 80,000.

REFERENCE 5

The viral infection inhibitory substance induced in the rabbit serum by the substance of this invention in accordance with the method shown in Reference 3, and that induced in the rabbit serum by Poly I:C in the positive control group were heated for one hour at 56°C.

Another group was adjusted with 1N HCl at pH 2.0 and left for one hour at 4°C. Still another group was treated by trypsin with the final concentration of 1,000 mcg/ml. at 37°C. for 3 hours.

As to the above test groups, the viral infection inhibitory activity was examined in line with Example 2. The result is summarized in Table 7.

As observed there, the viral infection inhibitory substance induced in the rabbit serum by this invention is stable to thermal treatment of 56°C. for one hour and to the acidic treatment of pH 2.0, and is protein which is susceptible to trypsin. Its properties are similar to those of inhibitory substance induced by Poly I:C. In this regard, the substance induced by the administration of the substance of the present invention is presumed to be interferon.

Table 7

| Treatment | Viral infection inhibitory activity (Dilution multiple of serum) | |
|---|---|---|
| | Substance of the present invention | Poly I:C |
| 56°c., 1 hour heating | 800 | 1,600 |
| pH 2.0, 4°C., 1 hour | 800 | 1,600 |
| Trypsin treatment 1,000 mcg/ml, 37°C., 3 hour | 100 | 1 |
| Non-treatment | 1,600 | 6,400 |

REFERENCE 6

By use of electrophoretic equipotential fractionation which is generally used in the measurement of equipotential point of protein, the equipotential point of viral infection inhibitory substance was examined, which was induced in the rabbit serum by the substance of this invention. Namely, 2 ml. of interferon-containing fraction obtained Sephadex G-100 gel filtration of Reference 4 was mixed into carrier amphorite of pH 5-8 by LKB Produkter AB, and using 110 ml. column, electrophoresis was made at 4°C., 700 volt and for 27 hours. Then, the fraction collector was effected as to each 2 ml. fraction and pH value of each fraction was measured.

Figure 5:
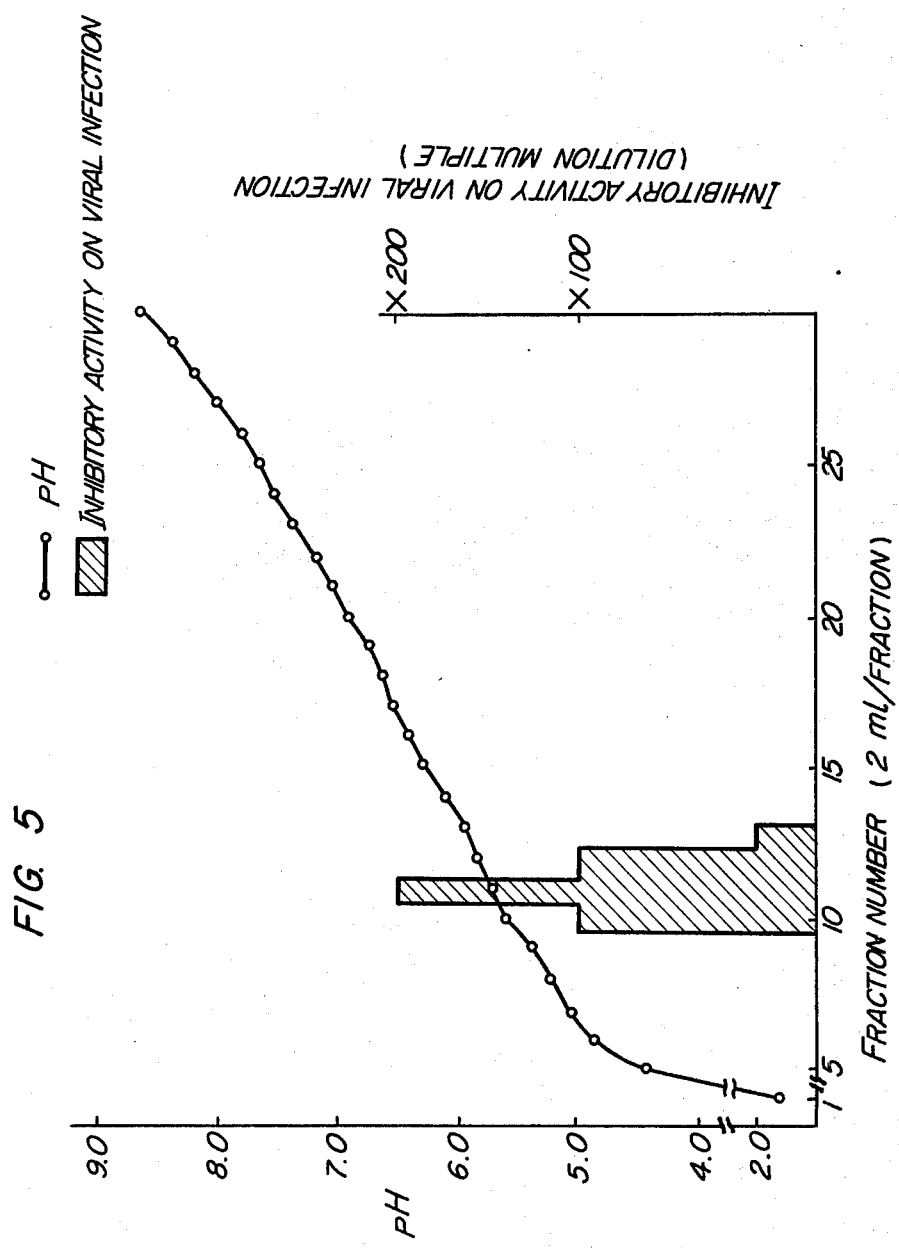

Each fraction was subjected to dialysis by use of a cellophane tube with 0.005 mol Tris-hydrochloric acid buffer solution containing 0.1 mol NaCl and 0.01 mol EDTA at 4°C. for 24 hours. Furthermore, those passed through the milipore filter were examined as to the viral infection inhibitory function of each fraction according to the method as described in example 2. The result is shown in FIG. 5.

As indicated there, the viral infection inhibitory substance found in the rabbit serum of this invention is considered protein which has the equipotential point at pH 5.7.

REFERENCE 7

In order to examine the biological properties of the substance of this invention, following experiments were conducted.

Twenty rabbits each weighing 2 kg., 20 mice each weighing ca. 20 g. and 20 chickens each weighing 800 g. were administered intravenously with the substance of this invention at the dosage of 500 mg/kg, 1 mg/kg and 400 mg/kg to the respective group of animals. 2 Hours after the administration, blood was taken from the heart of animal and subjected to the centrifugal separation for 5 minutes at 3,000 rpm. The serum of three kinds of animals was thus prepared.

On the other hand, 100 mg/ml of the substance of this invention was added for 8 hours at 37°C. to the primary cultured cells of rabbit kidney, mouse embryo and chicken embryo. Thereafter, the cells were washed sufficiently with Hanks' solution and cultivated further for 12 hours on the fresh medium to obtain 3 kinds of cell culture solutions.

As to the substance of this invention and the above serum or culture solution, the viral infection inhibitory effect was investigated using the primary culture cells of rabbit kidney, mouse embryo and chicken embryo in the same manner as described in Example 2, except that vaccinia virus was used in the mouse embryo cells. The result is shown in Table 8.

As indicated there, the viral infection inhibitory substance induced by the substance of this invention in the rabbit and its primary kidney culture cells has the resistance to the viral infection only in the primary cultured cells of rabbit kidney and shows no inhibitory activity to viral infection in the mouse embryo and chicken embryo cells. Similarly, the viral infection inhibitory substance induced in mouse and its embryo cells by the substance of this invention has the viral resistant activity only in mouse embryo cells. Accordingly, the viral infection inhibitory substance induced by the substance of this invention shows species specificity.

Table 8

| Animal or cell | | Viral inhibitory effect (Maximum effective dilution multiple) | | |
| --- | --- | --- | --- | --- |
| | | Rabbit kidney cell | Mouse embryo cell | Chicken embryo cell |
| Rabbit | Serum | 1,600 | <5 | <10 |
| | Culture fluid | 20 | <5 | <10 |
| Mouse | Serum | <10 | 50 | <10 |
| | Culture fluid | <10 | 10 | <10 |

What we claim is:

1. A pharmaceutical composition for viral infection inhibitory substance induction containing pharmaceutical carrier and as an active ingredient an effective amount of double stranded RNA substance prepared by extracting and isolating the double stranded RNA fraction out of the spore or mycelium of basidiomycetes.

2. A pharmaceutical composition according to claim 1, wherein the basidiomycetes is *Cortinellus Shiitake*.

3. Veterinary agent for viral infection inhibitory substance induction, containing a double stranded RNA substance which is obtained by extracting and isolating the double stranded RNA fraction out of the spore or mycelium of basidiomycetes.

4. Veterinary agent according to claim 3, wherein the basidiomycetes is *Cortinellus Shiitake*.

5. A process for producing pharmaceutical composition for viral infection inhibitory substance induction, which comprises adding to a pharmaceutical carrier an effective amount of double stranded RNA substance prepared by extracting and isolating the double stranded RNA fraction out of the spore or mycelium of basidiomycetes.

6. A process according to claim 5, wherein the basidiomycetes is *Cortinellus Shiitake*.

7. A method for inducing a viral infection inhibitory substance in the individual body which comprises administrating to a person, an animal or a bird an effective amount of double stranded RNA substance prepared by extracting and isolating the double stranded RNA fraction out of the spore or mycelium of basidiomycetes.

8. A method according to claim 7 wherein the administration is conducted intraperitoneally or intranasally.

9. A method according to claim 7, wherein the basidiomycetes is *Cortinellus Shiitake*.

* * * * *